(12) United States Patent
Meyer

(10) Patent No.: US 6,280,529 B1
(45) Date of Patent: Aug. 28, 2001

(54) ADHERENT WIPES AFFIXED TO GLOVES

(75) Inventor: Alvin Meyer, San Mateo, CA (US)

(73) Assignee: Darcy M. Dunaway, San Mateo, CA (US)

( * ) Notice: Subject to any disclaimer, the term of this patent is extended or adjusted under 35 U.S.C. 154(b) by 0 days.

(21) Appl. No.: 09/248,368

(22) Filed: Feb. 8, 1999

(51) Int. Cl.$^7$ ................................................. A47L 13/18
(52) U.S. Cl. ............................ 134/6; 15/227; 15/210.1
(58) Field of Search ........................... 15/104.002, 209.1, 15/210.1, 227, 244.1, 244.4; 139/6; 433/136; 604/386, 389

(56) References Cited

U.S. PATENT DOCUMENTS

| | | | |
|---|---|---|---|
| 1,006,741 | * 10/1911 | Ferry . | |
| 1,730,266 | * 10/1929 | Dailey . | |
| 2,249,936 | * 7/1941 | Birtcher | 15/210.1 |
| 2,651,071 | * 9/1953 | Dyer et al. | 15/227 |
| 2,763,885 | * 9/1956 | Lyons | 15/227 |
| 2,904,814 | * 9/1959 | Scholl | 15/244.1 |
| 3,231,918 | * 2/1966 | Marks | 15/227 |
| 3,885,249 | * 5/1975 | De Brabander | 15/227 |
| 4,212,296 | 7/1980 | Schaar . | |
| 4,285,338 | 8/1981 | Lemelson . | |
| 4,510,640 | * 4/1985 | Omori | 15/227 |
| 4,616,644 | 10/1986 | Safferstein et al. . | |
| 4,621,388 | * 11/1986 | Ortolivo | 15/104.94 |
| 4,635,624 | 1/1987 | Gilman . | |
| 4,645,251 | * 2/1987 | Jacobs | 15/227 |
| 4,667,666 | 5/1987 | Fryslie . | |
| 4,757,556 | * 7/1988 | Girard | 15/227 |
| 4,907,579 | 3/1990 | Kum . | |
| 4,966,595 | 10/1990 | Meringola . | |
| 5,074,293 | 12/1991 | Lott et al. . | |
| 5,079,792 | * 1/1992 | D'Haen | 15/227 |
| 5,180,360 | 1/1993 | Rhame . | |
| 5,280,664 | * 1/1994 | Lin | 15/227 |
| 5,328,449 | 7/1994 | Andrews et al. . | |
| 5,718,695 | 2/1998 | Keegan et al. . | |
| 5,820,578 | 10/1998 | Johansen . | |
| 5,833,646 | 11/1998 | Masini . | |

\* cited by examiner

*Primary Examiner*—Terrence R. Till
(74) *Attorney, Agent, or Firm*—Flehr Hohbach Test Albritton & Herbert LLP

(57) ABSTRACT

A laminated pad of gauze (10), cellulose, sponge (18), abrasive tiles or other functional materials, can be attached to a glove (14) or an affixed adhesive layer (12). A protective sheet (13) may be provided over the adhesive layer to protect it prior to use. The pad is attached, using the adhesive, to the back (15) of a glove or to garments or body surfaces or work surfaces. The pad is arranged to cleanse, wet or shape tool nibs and to hold small parts for future usage The pad can also be attached with a strap (32.

12 Claims, 2 Drawing Sheets

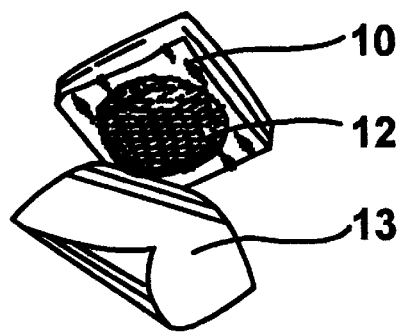
Fig. 1
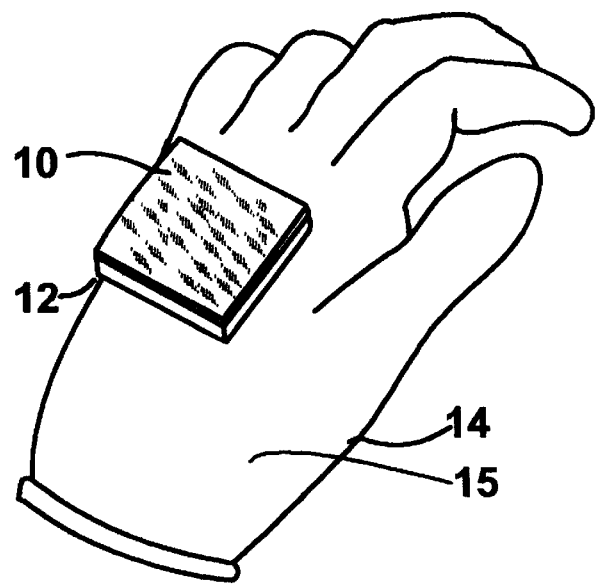
Fig. 3
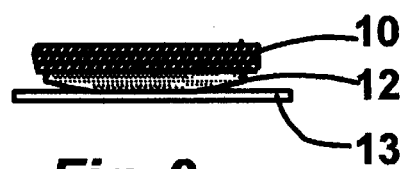
Fig. 2
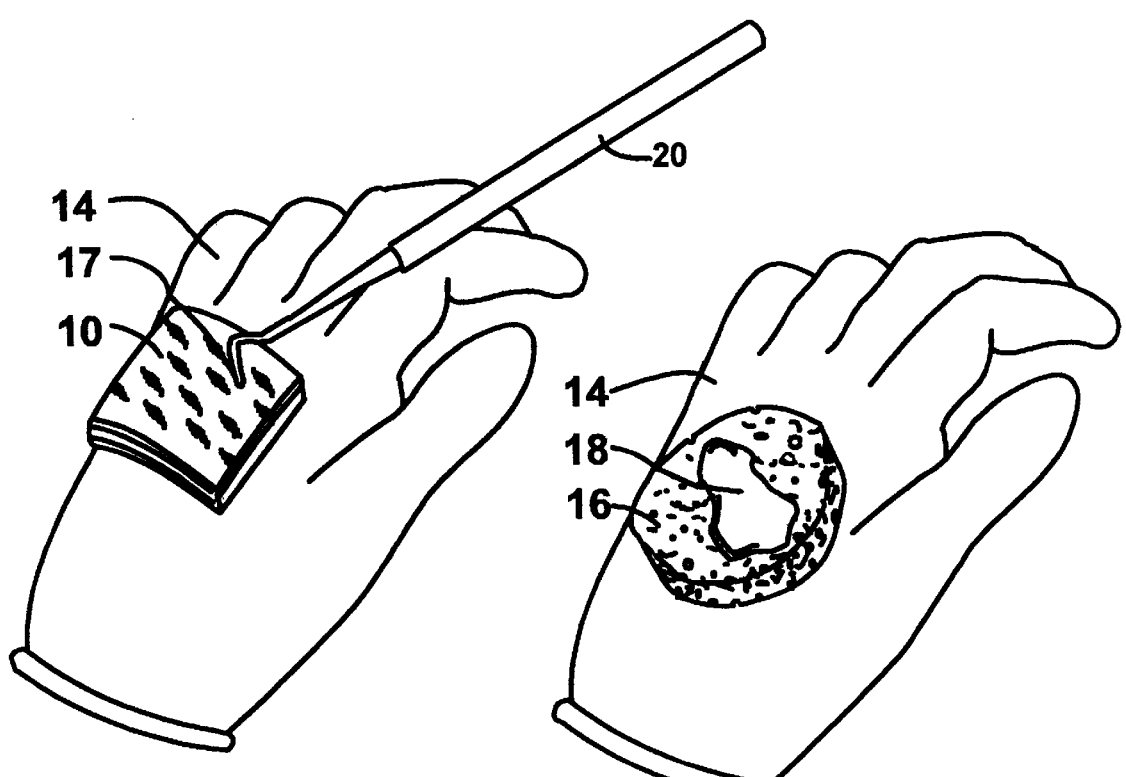
Fig. 4  Fig. 5

ADHERENT WIPES AFFIXED TO GLOVES

BACKGROUND—FIELD OF THE INVENTION

This invention relates to the cleaning and conditioning of tools and instruments, specifically to a device for such cleaning and conditioning which may be used more efficiently and easily.

BACKGROUND—DESCRIPTION OF THE PRIOR ART

Workers, technicians, and professionals such as surgeons, sculptors, solderers, dentists, and others use tools and instruments which become contaminated with fluids, debris, and other substances in the course of their work. Often, both hands are used to manipulate the instruments or the instrument and the treated object. To clean the instrument, one hand must release the object being held for modification, lift wiping material to and wipe the instruments, and then return the wipe, forcing ones eyes to leave the working field and then reorient. For example, a dentist may use a scraper which then becomes contaminated with hardened material scraped from a tooth. The dentist must frequently wipe the accumulated calculus off to continue using the curette effectively. This diversion is disadvantageous and even dangerous since the work must be interrupted and the patient ignored temporarily.

Workmen who solder fine components frequently clean hot iron tips on sponges. Sculptors carving wax, clay, plastic, or wood must dispose of the material which adheres to tools to maintain good visibility.

Various prior-art references show devices which are relevant to, but do not solve, the problems of inconvenience, interrupted visibility, and time losses. U.S. Pat. No. 4,212,296 to Schaar (1980) reveals a bandage covered by an adhesive strip for its attachment but does not expose a surface suitable for wiping. U.S. Pat. No. 4,285,338 to Lemelson (1981) discloses a rigid bandage attached by an outer adhesive tape which again exposes no utilitarian surfaces. U.S. Pat. No. 4,966,595 to Meringola and Lo Duca (1990) exposes a surgical sponge of multi-layered gauze which may be attached to a wound by the awkward expedient of joining twill tie-down strips. U.S. Pat. No. 5,328,449 to Andrews et al. (1994) shows a glove with multiple layers of gauze internally positioned to absorb moisture, but again provides no exposed wiping surface. U.S. Pat. No. 5,820,578 to Johansen (1998) discloses a bandage which may be affixed over a wound by use of adhesive tabs on its outer exposed surfaces. However, this bandage lacks the simplicity and economy required by most workers. 3M and others manufacture cellulose adhesive tapes which may be used to tape a pad's edges to an appropriate surface but such procedures are laborious and time-demanding.

OBJECTS

Accordingly, several objects and advantages of the present invention are:

(1) to provide a way in which users of instruments and tools can more conveniently wipe them,
(2) to provide a wiping device with which the operator can see the wipe surface without losing any view of or orientation toward the treated object,
(3) to provide a wiping device with which the operator may continue to hold the treated object while wiping,
(4) to provide a wiping device with which collaborating operators may share the same wipe,
(5) to provide a wiping device with which an enchant, lubricant, or pigment may be added to an absorbent pad for subsequent delivery to the tool,
(6) to provide a wiping device with which any valuable material, removed as excessive, may be reclaimed, and
(7) to provide an easy-to-use abrasive or honing surface for dressing tool surfaces. Still further objects and advantages will become apparent from a consideration of the ensuing description and drawings.

Further objects and advantages are to provide multiple functional surfaces in positions within the visualized treatment field and to provide a device which is advantageously useful:

DRAWING FIGURES

In the drawings, closely related figures have the same numbers.

FIG. 1 shows an isometric view of a wiping pad, having an applied adhesive layer, and a protective film being removed to reveal the adhesive, in accordance with the invention.

FIG. 2 shows an end sectional view of layered pad of FIG. 1, its adhesive layer and its protective film, in accordance with the invention.

FIG. 3 shows a view of a glove with an affixed wipe, in accordance with the invention.

Fig. 4 shows an instrument positioned to use the wipe and glove combination of FIG. 3, in accordance with the invention.

FIG. 5 shows a wipe of sponge, plastic sponge, leather, abrasives or demagnetizing material affixed to a glove, in accordance with the invention.

Figure 6:
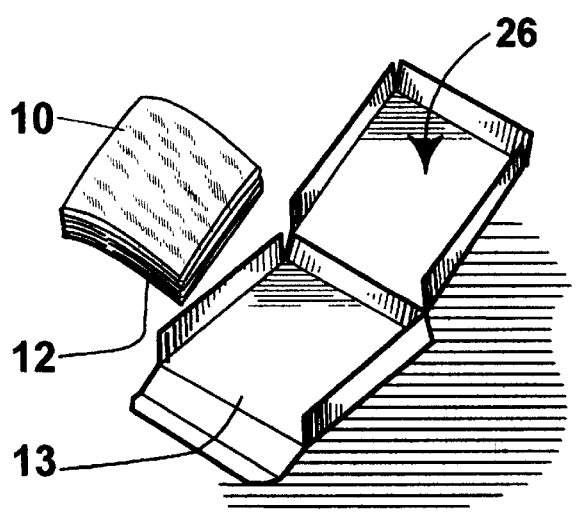
FIG. 6 shows an isometric view of a thin paper container with protective film affixed to the inner surfaces to avoid adherence of the wipe to the container, in accordance with the invention.

REFERENCE NUMERALS 10 pad, gauze
11 abrasive substance
12 adhesive
13. protective film
14 glove or bare hand
15 dorsal surface of a hand or glove or alternative surface.
17. tool, worldng nib
18. fluid additive
19. abrasive groove for shaping a nib
20. abrasive tile, stropping leather or abrasive paper
32. elastic band
34. free end of elastic band 32

DESCRIPTION FIG. 1–3

FIG. 1 shows a laminated assembly comprising a gauze pad 10 of fabric, steel wool, fiberglass, leather, or abrasive with an adhesive 12 applied to its undersurface and film 13 of metal foil, plastic, or treated paper to protect the adhesive layer until it is used. The assembly in this embodiment is rectangular and about 2.5 cm×2.5 cm×3 mm, but numerous applications will require other dimensions.

In the preferred embodiment, adhesive layer 12 is imprinted upon protective sheet 13 and then applied to wipe component 10. In other embodiments the undersurface may be impregnated with adhesive 12 applied by spraying or rolling over wipe 10. In another manufacturing procedure adhesive 12 is applied to both surfaces of a film which is interposed between wipe 10 and protective sheet 13.

FIG. 2 is a cross-sectional view of the laminated assembly, demonstrating the layered configuration of wipe 19, adhesive 12, and protective sheet 13. The dimension of adhesive 12 is smaller than wipe 10 to avoid any adherence to the sidewalls of its shipping container as shown in Fig. 6. Also, the free edges facilitate the removal of the wipe when it is peeled from supportive surface 14 or from protective sheet 13, In FIG. 3 wipe 10 with protective film 13 removed, the pad has been pressed to the back of a glove 14 so that adhesive 12 will attach wipe 10, sponge, 16 or hone 18 to supportive or dorsal surface 15 on the back of glove 14.

The absorbent pad of the invention may be formed of twisted paper, laminated cotton gauze, cellulose bars, leather or any similarly absorbent materials.

In an embodiment wherein the glove is formed of surgical latex, the gauze pad may be applied while the latex film remains liquid. In its other embodiments, contact adhesives such as Super 77 Spray Adhesive from 3M Adhesives may be applied as a sprayed liquid or a double-stick film to the under surface of a pad. The adhesive will be protected by a removable non-adherent film or a wax-like application to the inner surfaces of its container.

Operation—FIG. 4

FIG. 4 is a view of a nib 17 of an instrument 20 being wiped on pad 10. In usage, pad 10 is removed from wrapper 26 or protective sheet 13 to expose adhesive underface 12. The laminated assembly is affixed to a dorsum 15 or a selected nearby surface. Nib 17 is wiped across pad 10 as the work proceeds. Since pad 10 is on the back of the user's hand or a very nearby surface it is within the operator's field of vision at all times and may become a memorized position which can be utilized without diverting one's eyes DESCRIPTION AND OPERATION—FIG. 5 and 6

FIG. 5 shows a thick pad 16 of sponge for.receiving and delivering fluids to an instrument.

In usage, pad 16 is removed from a box or other wrapper 26 (FIG. 6) or protective sheet 13 (Fig. 1) to expose adhesive layer 12. The assembly is affixed to dorsum 15 (FIG. 3) or a selected nearby surface. A fluid 18 (FIG. 5) such as lubricants, antiseptics, etchants, adhesives or the like is dropped upon the exposed surface of pad 16. As the work proceeds, nib 17 will be wiped across wet pad 16 to supply fluid to the nib to be transported to the work site.

Figure 7:
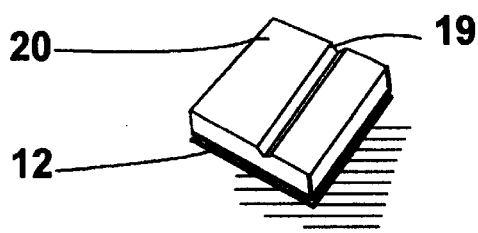
FIG. 7 shows an isometric view of a honing tile having a groove to grind or sharpen a predetermined shape onto the nib, in accordance with the invention.

Abrasive tile 20 (Fig.7) presents a surface suitable for honing a cutting edge or reshaping a surface of a nib. The facet which provides the cutting edge may be scraped upon the flat surface to be reconditioned. Groove 19 is shaped to provide a predetermined configuration to the cutting facet of the nib when the nib is sharpened by scrubbing along its length.

Figure 10:
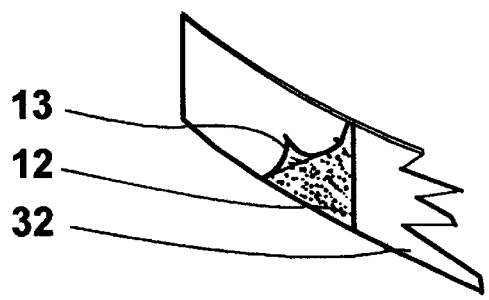
FIG. 10 shows one end of the elastic band with an adhesive zone and protective sheet to enable the forming of a retentive elastic circle, in accordance with the invention.
Figure 11:
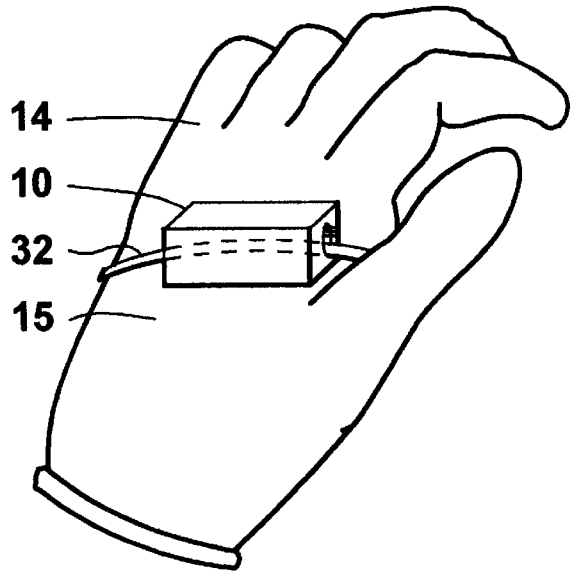
FIG. 11 shows the wipe and its circular elastic retainer in position on a gloved hand, in accordance with the invention.

Pad 10 (FIG. 9–11) is held in position on the dorsum or wrist by a cord, ribbon or elastic retainer 32 (FIG. 9–11) which may be adjusted for size by cementing 12 (FIG. 10) the free ends together using adhesive layer 12 (FIG. 10) or a continuous elastic retainer band may be provided which will require no cement. Pad 10 is retained in view and available for wiping, honing or wetting an instrument.

Figure 8:
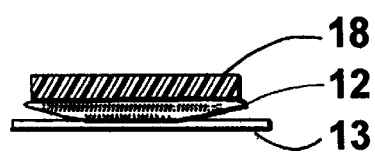
FIG. 8 is an edge view of tile, adhesive and protective film of FIG. 7, in accordance with the invention.

Tile 18 (FIG. 8) has contact adhesive 12 on its underside protected by a non-adherent film 13. After removal of the protective film, tile 18 is affixed to a chosen surface or a part of the operator's garments or person to be available for reconditioning in a convenient location.

DESCRIPTION AND OPERATION—FIGS. 9–11

Figure 9:
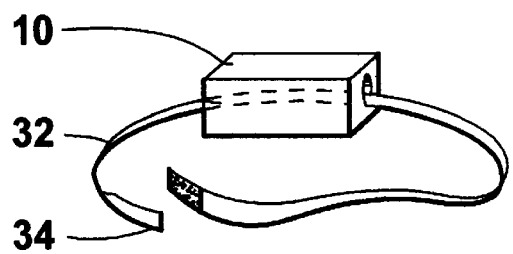
FIG. 9 shows a wipe with an attached, dimensionally adjustable elastic to encircle the hand, wrist, or other object, in accordance with the invention.

FIG. 9, shows a strap-on wipe. An elastic band 32 penetrates through a hole in pad 10 as shown in FIG. 9 or is affixed to wipe 10 by adhesives or welding. One terminus of the elastic band 32 has a contact adhesive 12 added to a limited area and is protected by a removable film 13 to facilitate its attachment to the other free end 32. In use, the free ends of the band is wrapped around a supportive object 15 such as glove 15 and its ends are joined to form a retentive circle. The operation of this embodiment is similar to that of FIGS. 4 and 5.

The pad may be formed of sponge, laminated gauze, crushed paper or sponge-like plastics and may be used as a convenient delivery system for liquids, lubricants, pigments or medicaments. Sculptors frequently wet their carving tools to obtain a smoother cut. Watchmakers lubricate components. Glass cutters often lubricate the carbide cutting wheels they use. My pad arrangement facilitates and speeds the delivery of the fluid to the instrument without distracting the operators eyes from the working field.

SUMMARY RAMIFICATIONS, AND SCOPE

Accordingly, the reader will see that, according to the invention, I have provided supplementary surfaces, for application to a glove, garment or any other nearby surface which will afford conveniently positioned surfaces for whetting, cleaning or modifying a nib, brush, pencil or the like. Such whetting, cleaning, or modifying may be performed without distracting the worker's view of the treatment field and with a minimum of expended effort. The worker can continue to hold a treated object or supplementary instrument with the same hand that bears the wipe. Coworkers may share the same wipe.

Further, absorbent surfaces may be affixed which can be saturated with chemicals required for the operation at hand. An etchant, lubricant or pigment may be added to an absorbent pad for subsequent delivery to the tool.

Workers who trim gold castings or work with other valuable materials may conveniently reclaimed trimmed excess by wiping the trimmings upon a pad which will then have resale value. For example, in one embodiment the wiping pad is adhesive so that it can collect and recover valued trimmings.

Small parts like pins, screws of watch components may be inserted into the pads to be quickly retrieved. A replacement of pads and sponges with receptacles will provide a handy storage position for small parts.

The elastic band may be replaced with a ribbon of fabric or string.

The elastic band, made discontinuous for size adjustability, may have a continuous band.

Dentists frequently find that their curettes and chisels need to be resharpened. A honing tile affixed to the back of his hand will provide an opportunity to dress the edges without losing view of the working field.

Two or more of the pads may be affixed to the same surface to do cleansing, wetting or honing in the same area.

While the above description contains many specificities, these should not be construed as limitations on the scope of the invention, but merely as illustrations of several presently preferred embodiments. Many other variations are possible. For example, the pad may have a portion of its surface as an absorbent wipe and the remaining portion as an abrasive or sponging surface. Adherent sponges can be supplied in waterproof containers with medicaments or other liquids already in the sponge. Adherent sponges may be divided by partitions to deliver various fluids.

Thus the scope of the invention should be determined by the appended claims and their logical equivalents, rather than by the examples given.

The band of FIG. 9 can be non-elastic and can have hook-and-loop fastening material, snaps, hooks or other end fasteners such as pins. Alternatively, the band and pad may be applied to an ungloved hand, arm, leg or torso and may be affixed to nearby work surfaces.

I claim:

1. A device for use in performing a dental, medical or surgical procedure, said device comprising;
   a wiping pad,
   a thin-walled glove suitable for use in a dental, medical or surgical procedure and adapted to be worn on a band of a user, said glove including fingers, a back side and a wrist,
   means attaching said wiping pad to said back side of said glove between said fingers and said wrist, whereby the user can conveniently and rapidly wipe a tool or instrument during the procedure.

2. The device of claim 1 fther comprising an adhesive layer on a bottom surface of said wiping pad adhering said pad to said glove.

3. The device of claim 1 wherein said glove is a latex or vinyl glove and said pad is adhered to said glove while it is being formed and while the latex or vinyl is still moist.

4. The device of claim 1 wherein said wiping pad is moistened.

5. The device of claim 1 wherein said wiping pad is abrasive so that it can reshape or hone said tool or instrument.

6. The device of claim 1 wherein said wiping pad is adhesive so that it can collect and recover valued trimmings.

7. A method for performing a dental, medical or surgical procedure, said method comprising:
   providing a wiping pad and a thin-walled glove suitable for use in a dental, medical or surgical procedure and adapted to be worn on a hand of a user,
   attaching said pad to a back side of said glove,
   wiping a tool or instrument on an exposed surface of said wiping pad,
   whereby said user can conveniently and rapidly wipe the tool or instrument during the procedure without having to look away from a work area.

8. A device for use in performing a dental, medical or surgical procedure said device comprising a wiping pad and an elastic member adapted to be worn around a hand of a user during the procedure with said wiping pad superimposed above the back of the hand between fingers and a wrist of the hand allowing the user to conveniently and rapidly wipe a tool or instrument during the procedure, wherein said wiping pad is adhered to said elastic member while said elastic member is being formed.

9. The device of claim 8 wherein said elastic member is thin-walled glove suitable for use in a dental, medical or surgical procedure.

10. The device of claim 8 wherein said elastic member is a latex or vinyl glove, wherein said wiping pad is adhered to said glove while it is being formed and while the latex or vinyl is still moist.

11. A glove for use in performing a dental, medical of surgical procedure, said glove comprising:
    a wiping pad having a planar working area,
    a glove suitable for use in a dental, medical or surgical procedure and adapted to be worn on a hand of a user, said glove including fingers, a backside and a wrist
    means attaching said wiping pad to said back side of said glove between said fingers and said wrist, whereby the user can conveniently and rapidly wipe a tool or instrument on said working area during the procedure.

12. The glove of claim 11 wherein said working area is substantially parallel to a substantially planar surface of a back of the hand.

* * * * *